US005743266A

United States Patent [19]
Levene et al.

[11] Patent Number: 5,743,266
[45] Date of Patent: Apr. 28, 1998

[54] METHOD FOR PROCESSING REAL-TIME CONTRAST ENHANCED ULTRASONIC IMAGES

[75] Inventors: Harold Levene, San Diego; Bob Webster, Carlsbad, both of Calif.

[73] Assignee: Molecular Biosystems, Inc., San Diego, Calif.

[21] Appl. No.: 428,723

[22] Filed: Apr. 25, 1995

[51] Int. Cl.$^6$ ...................................................... A61B 8/00
[52] U.S. Cl. ...................................................... 128/662.02
[58] Field of Search ........................ 128/660.01, 662.02, 128/660.07, 660.05, 654, 653.4

[56] References Cited

U.S. PATENT DOCUMENTS

| | | |
|---|---|---|
| 4,802,093 | 1/1989 | Ema . |
| 5,027,413 | 6/1991 | Barnard . |
| 5,235,984 | 8/1993 | D'Sa ........................... 128/660.07 |
| 5,255,683 | 10/1993 | Monaghan ..................... 128/662.02 |
| 5,425,366 | 6/1995 | Reinhardt et al. ............... 128/662.02 |
| 5,457,754 | 10/1995 | Han et al. . |
| 5,469,849 | 11/1995 | Sasaki et al. .................. 128/660.07 |
| 5,476,096 | 12/1995 | Olstad et al. .................. 128/660.07 |

FOREIGN PATENT DOCUMENTS

| | | |
|---|---|---|
| 0521559 | 1/1993 | European Pat. Off. . |
| A 07 059 781 | 3/1995 | Japan . |
| 84/02838 | 8/1984 | WIPO . |
| 91/19457 | 12/1991 | WIPO . |
| 93/12720 | 7/1993 | WIPO . |

OTHER PUBLICATIONS

Bates et al., "Color Coding of Digitized Echocardiograms: Description of a New Technique and Application in Detecting and Correcting for Cardiac Translation," *J. Am. Soc. Echocardiography*, 7(4): 363-369 (1994).

Crooks et al., "A Novel Algorithm for the Edge Detection and Edge Enhancement of Medical Images," *Med. Phys.*, 20(4): 993-998 (1993).

Feigenbaum, *Echocardiography*, pp. 68-90 5th Ed (1994).

Geiser et al., "A Second-generation Computer-based Edge Detection Algorithm for Short-axis, Two-dimensional Echocardigraphic Images: Accuracy and Improvement in Interobserver Variability," *J. Am. Soc. Of Echocardiography*, 3(2): 79-90 (1990).

Halmann et al., "Digital Subtraction Myocardial Contrast Echocardiography: Design and Application of a New Analysis Program for Myocardial Perfusion Imaging," *Journal of the American Society of Echocardiography*, 7(4): 355-362 (1994).

Hwang et al., "Multilevel Nonlinear Filters for Edge Detection and Noise Suppression," *IEEE Transactions on Signal Processing*, 42(2): 249-258 (1994).

(List continued on next page.)

*Primary Examiner*—Francis Jaworski
*Attorney, Agent, or Firm*—Morrison & Foerster

[57] ABSTRACT

The present invention is a novel method for producing real-time colorized, contrast enhanced images from a sequence of grey-scale video images obtained during diagnostic ultrasound. The particular colorizing scheme varies according to which information parameter is desired to be displayed in real-time. The information parameters used to colorize a segment of video images include: time-to-arrival, duration of brightening, and absolute brightening. Time-to-arrival colorization depicts the time that a given pixel achieves a given intensity threshold. Duration of brightening depicts the time that a given pixel's intensity stays above a given threshold. Absolute brightening depicts various threshold values obtained by the region's pixels.

38 Claims, 16 Drawing Sheets

(9 of 16 Drawing(s) in Color)

OTHER PUBLICATIONS

Maes et al., "Automated contour Detection of the Left Ventricle in Short Axis View and long Axis View on 2D Echocardiograms" *Proceedings. Computers in Cardiology* Cat. No. 90CH3011–4 pp. 603–606 (1990).

Sebastiani et al., "Analysis of dynamic magnetic resonance images," *IEEE Transactions on Medical Imaging* 15(3): 268–277 (1996).

Unser et al., "Automated extraction of serial myocardial borders from M–mode Echocardiograms," *IEEE Transactions on Medical Imaging* 8(1) 96–103 (1989).

Vinning et al., "Receiver Operating Characteristic Curves: A Basic Understanding." *Radiographics*, 12(6): 1147–1154 (1992).

*Echocardiography in Coronary Artery Disease*, Chapter 22, pp. 483–508, E.A. Geiser: "Applications of Automatic Edge Detection and Image Enhancement Techniques to Two–Dimensional Echanography and Coronary Disease," (R.E. Kerber ed., Mount Kisco, New York: Futura Publishing Co. 1988).

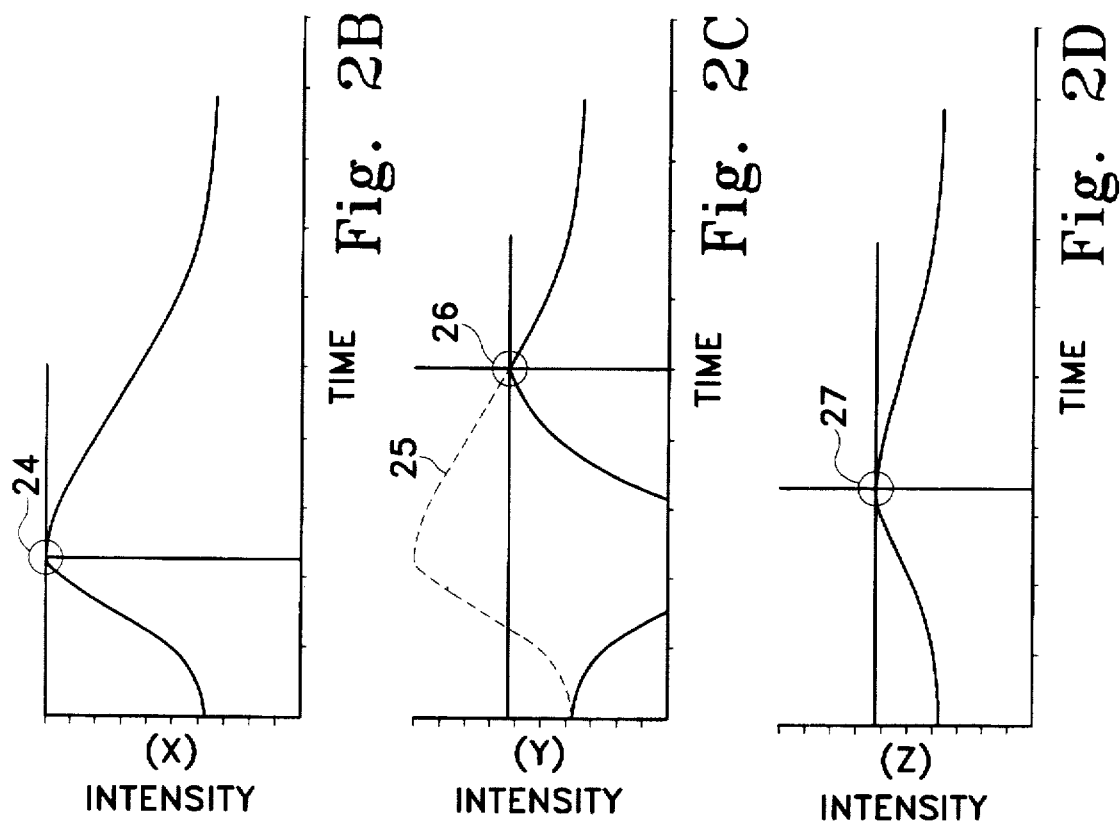
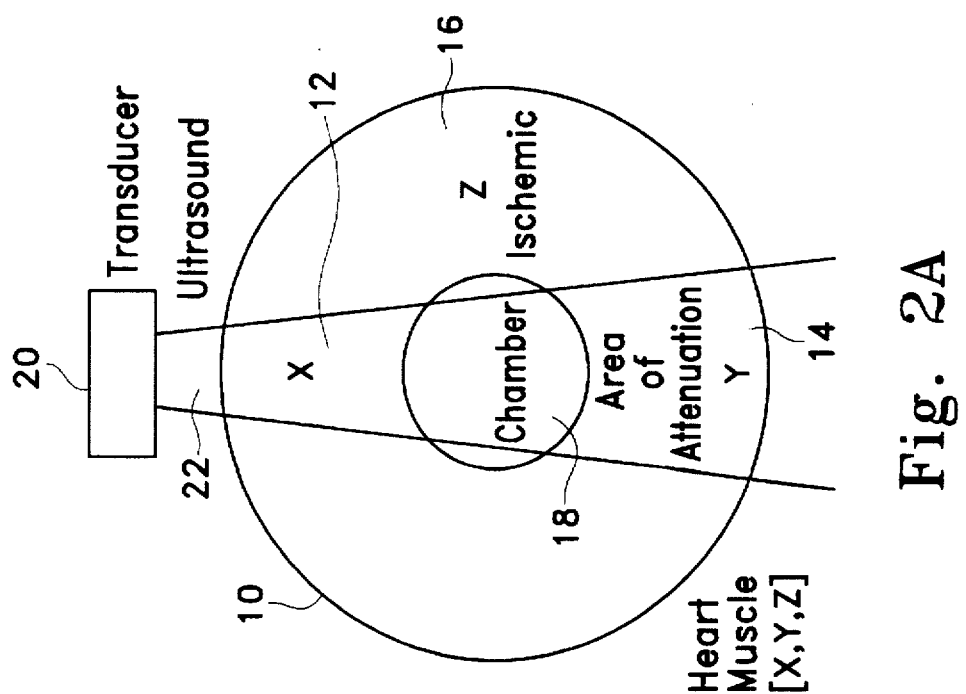

1

METHOD FOR PROCESSING REAL-TIME CONTRAST ENHANCED ULTRASONIC IMAGES

FIELD OF THE INVENTION

The present invention relates in general to a method for processing a sequence of contrast-enhanced ultrasonic images and, in particular, to a method for colorizing a sequence of diagnostic ultrasound images in real-time which are characterized by one or more parameters.

BACKGROUND OF THE INVENTION

In the field of medical diagnostic imaging, it is known to produce images of a patient's organs/tissues and to analyze these images for the express purpose of identifying potential disease conditions. For this purpose, there is a number of diagnostic modalities that may be used to obtain such images. For example, it is known to use single photon emission computed tomography ("SPECT"), positron emission tomography ("PET"), computed tomography ("CT"), magnetic resonance imaging ("MRI"), angiography and ultrasound. An overview of these different modalities is provided in: Cardiac Imaging—A Companion to Braunwald's Heart Disease, edited by Melvin L. Marcus, Heinrich R. Schelbert, David J. Skorton, and Gerald L. Wolf (W. B. Saunders Co., Philadelphia, 1991)

One modality that has found particular usefulness is contrast enhanced ultrasound imaging. Briefly, this technique utilizes ultrasonic imaging, which is based on the principle that waves of sound energy can be focused upon a "region of interest" ("ROI") and reflected in such a way as to produce an image thereof. The ultrasonic transducer utilized is placed on a body surface overlying the area to be imaged, and sound waves are directed toward that area. The transducer detects reflected sound waves and the attached scanner translates the data into video images. The quality of the images produced are further enhanced by the use of a contrast agent during the imaging session.

When ultrasonic energy is transmitted through a substance, the amount of energy reflected depends upon the frequency of the transmission and the acoustic properties of the substance. Changes in the substance's acoustic properties (e.g. variance in the acoustic impedance) are most prominent at the interfaces of different acoustic density or compressibility, such as liquid-solid or liquid-gas. Consequently, when ultrasonic energy is directed through tissue, organ structures generate sound reflection signals for detection by the ultrasonic scanner. These signals can be intensified by the proper use of a contrast agent.

Contrast enhanced images have the property that the presence of contrast in a particular ROI produces an image visually recognizable from surrounding regions that are not suffused with the agent. One example of this type of imaging is myocardial contrast echocardiography ("MCE"). In MCE, an intravascular injection of a contrast agent washes into the patient's heart while, simultaneously, ultrasound waves are directed to and reflected from the heart—thereby producing a sequence of contrast enhanced echocardiographic images.

Conventional ultrasound imaging is termed B-mode or "grey scale" and the shades of grey are based upon the amplitude of the backscatter which is transmitted back to the transducer from each ROI. The employment of contrast agents aids in grey scale imaging by increasing the backscatter in a particular region as a result of the introduction of a contrast agent having increased echogenicity. The areas in which the contrast agent is present will appear brighter in a grey scale image.

In connection with ultrasound imaging, "backscatter" is a measure of the echogenicity of a particular substance (i.e. tissue, contrast agent, and the like). Backscatter coefficient is an independent measure of the echogenicity of a substance. The degree of amplitude of backscatter observed is dependent on incident intensity.

"Attenuation" is a measure of the scattering, reflection, and absorption of the ultrasonic energy by a particular substance whereby less of the energy passes entirely through that substance and beyond. If the ultrasound energy is significantly attenuated during its transmission through a substance, it will diminish the backscattering signal posterior to that substance thereby causing the posterior region to appear dark, regardless of the backscatter coefficient of material in that region. This is termed "shadowing." The shadowing effect causes portions of the grey scale image to appear dark when, in fact, there actually is contrast agent present in the tissue. Significant attenuation does not allow for true visualization of the contrast agent which appears in the tissue/organs beyond the attenuating areas, and can lead to a false diagnosis.

The attenuation effect can lead to misinterpretation of the data when images are post-processed. For example, the effect of attenuation on the posterior myocardial wall is clearly evidenced in FIGS. 1A and 1B. In each of the frames, the transducer is located at the apex of the sector. In FIG. 1A, the entire myocardium is visible. However, with the introduction of the contrast agent into the chamber in FIG. 1B, the posterior region becomes dark, even though it may actually be experiencing some degree of perfusion with the agent.

FIGS. 2A–2D depict the problems associated with attenuation and how it may adversely impact the ability to make an accurate diagnosis. FIG. 2A is a top cross-sectional view of heart muscle 10 being imaged by ultrasound waves 22 emanating from transducer 20. Heart muscle 10 comprises three regions of interest—anterior region 12 (i.e. closest to the transducer and in front of heart chamber 18), lateral region 16, and posterior region 14 (i.e. furthest away from transducer 20 and where heart chamber 18 is positioned between region 14 and transducer 20.) These three myocardial regions 12, 14, and 16 are labelled for convenience sake as regions X, Y, and Z respectively. As the contrast agent washes in to the chamber, the agent absorbs and reflects much of the ultrasound energy, preventing it from reaching region Y. Regions X and Z are unaffected by the attenuation.

From the detected wave reflections, graphs, such as shown in FIGS. 2B–2D, may be generated. These graphs represent the mean image intensity of a particular ROI as a function of time. Thus, in FIG. 2B, a typical time-intensity curve is shown for heart anterior region X. From time at zero (i.e. the extreme left hand side of the graph) to maximum 24, the increasing portion of this graph is due to the wash-in of contrast agent into anterior region X. At maximum 24, the anterior region X reaches its greatest concentration of contrast agent. From maximum 24 until time at infinity, the gradual decreasing intensity is due primarily to the wash-out of contrast agent (i.e. decreasing concentration of contrast agent as the heart pumps through blood not imbued with contrast agent) from anterior region X. The time-intensity curve for the region of interest indicates that region X is normal, healthy tissue.

FIG. 2D depicts lateral region Z of heart 10 that might be characterized by a disease condition, such as ischemia, where the blood circulation to tissue in region Z is less than optimal. Because the blood flow is not optimal, it can be seen that maximum 27 is lower than the maximum 24 in region X and that the time to maximum in region Z is greater than the time to maximum in region X. Region Z, known to be unaffected by attenuation, shows a delay in both the time and intensity of the contrast agent. This indicates an abnormality in that ROI.

The time-intensity graph in FIG. 2C, although similar to the graph in FIG. 2D, exhibits the effects of shadowing, resulting from attenuation. Assuming that posterior region Y is as healthy as region X, the "actual" profiles of intensity should be approximately the same—attenuation effects excepted. Thus, if region Y were anterior as opposed to posterior to the transducer, one would expect dotted profile 25 to appear as the time-intensity curve. However, in actuality, as the anterior chamber 18 fills with contrast agent prior to perfusion in anterior region Y, the contrast agent in chamber 18 attenuates most of the ultrasound energy that might have penetrated and scattered off of region Y once it has perfused. Thus, as seen in FIG. 2C, the intensity of region Y drops off to almost zero regardless of whether perfusion occurs in that region. Region Y shows the effect of attenuation on otherwise healthy tissue.

At some time after chamber 18 reaches its maximum concentration of contrast agent, the effects of attenuation begin to wear off and the intensity in region Y begins to increase. However, a trained diagnostician would note that the maximum intensity in region Y is lower than for region X and occurs later in time than for region X. This response is similar to the response given for diseased region Z. Thus, the potential to falsely diagnose region Y as diseased—while merely witnessing the effects of attenuation—exists.

While colorization of ultrasound images has previously been used to determine where contrast agent may have appeared in the tissues, these uses have not effectively dealt with the problems of attenuation. In the article entitled "Quantification of Images Obtained During Myocardial Contrast Echocardiography", published in *Echocardiography: A Journal of CV Ultrasound & Allied Tech.* (Vol 11, No. 4, 1994), pages 385–396, authors Jayaweera et al. review methods of quantifying two-dimensional grey scale echocardiographic images obtained during MCE. Specifically, Jayaweera et al. disclose methods for obtaining time-intensity curves from MCE images. As well, they discuss enhancing images by means of color-coding algorithms that reflect the degree and extent of enhancement.

Color-coding techniques that helpful for visualizing the degree and extent of enhancement for a diagnostician, because the human eye is only able to discern a limited number of shades of grey, but has a much greater capacity to discriminate between various colors. To accomplish this, Jayaweera et al. digitally subtract pre-contrast images from contrast-enhanced images. In their preferred mode, three gated pre-contrast images are aligned and then averaged. The same is done for three gated contrast-enhanced images. The averaged pre-contrast image is then subtracted from the averaged contrast-enhanced image to yield one final post-processed frame.

For MCE color-coding, Jayaweera et al. have the operator define the endocardial and epicardial outlines in the digitally subtracted image. A histogram of grey scale intensities is then generated from the myocardial region within these outlines, and the digitally subtracted image is re-scaled over the entire dynamic range of the computer system followed by color coding. The color-coding operation is performed only within the myocardium defined by the endocardial and epicardial boundaries.

Thus, colorization in Jayaweera et al. is used primarily as a post-processing step after all video images have been captured. It is based upon the digital subtraction of pre-contrast from post-contrast frames and not upon time-intensity curves. This method may be used to create an end image which shows areas where contrast agent either did or did not appear.

In an article entitled "Digital Subtraction Myocardial Contrast Echocardiography: Design and Application of a New Analysis Program for Myocardial Perfusion Imaging", published by the *Journal of the American Society of Echocardiography*, July-August 1994, pages 355–362, authors Halmann et al. describe another method for color-coding video echocardiographic images by first obtaining a simple time-intensity curve and then calculating and color-coding various parameters. The time-intensity data generated reflects the wash-in, peak and the wash-out rates (i.e. that portion of the time-intensity curve prior to, during and after maximum intensity, respectively) of contrast-agent enhanced blood from a particular ROI. Once time-intensity data is captured from the set of images, Halmann et al. use this data to extract several parameters that enable evaluation of the ROI. Such parameters include: the slope of the curve at any point; maximum intensity and the time to achieve it; the width of the time-intensity curve; and the area under any defined region of the curve. These parameters may be used to quantify the extent of blood flowing through the ROI.

The method disclosed by Halmann et al. is similar to that described by Jayaweera et al. in that the colorization is done as a post-image capture processing step—i.e. after all frames have been recorded and digital subtraction of the frames of interest has been accomplished; thus, yielding a single, colorized image as an end-result. Neither of the two methods described capture the useful parameters which can only be appreciated by viewing processed images in real-time.

By using colorization merely as a static, post-capture processing step, very valuable information is lost that might otherwise be useful to detect dynamic tissue/organ function and conditions. These dynamic conditions may be noticeable only by viewing real-time colorized video sequences. One example of such a dynamic variable is "time-of-arrival" data—i.e. visual data showing the actual arrival time of contrast perfusion into a ROI in a particular organ. The time of arrival is an important diagnostic parameter as it may be used to identify a clinically significant stenosis of an artery. In such a case, there is a reduced blood flow rate through the artery, so that the contrast agent appearance is delayed in reaching the ROI.

Without a "time-of-arrival" parameter, the problem of attenuation is not likely to be noted, as in a single post-processed colorized image. This is especially true for the prior colorization methods of Halmann et al. because their time-intensity curves have been averaged over a region and may include portions of the region which are artificially low or late due to the attenuation effect.

Colorization performed according to the methods described by Jayaweera et al. or Halmann et al. do not adequately compensate for attenuation and its effects. Neither of the two prior methods describe any provision for detecting shadowing. Therefore, colorization of a shadowed region is not colored in a different manner from a non-shadowed region. For example, colorization by arrival time would color a shadowed region and an ischemic region similarly, although the reasons for the delay in appearance in the two regions are quite different. Thus, a trained cardiologist might falsely conclude that myocardial function is outside of normal parameters.

Real-time colorized video aids in the spotting of attenuation by 1) the ability to view the tissue prior to the introduction of the contrast agent; and 2) the simultaneous shadowing of the posterior tissue as the contrast agent washes into the chamber region. While viewing the images in real-time, it is possible to see the first frames and note the appearance of the tissue just prior to the arrival of the contrast agent. A subsequent rapid decrease in the brightness of the tissue concurrent with the wash-in of the contrast agent into the chamber would be recognized as the result of attenuation and not of tissue abnormality. Without the ability to see these two things, as is lacking in a single post-processed frame, the clinician would have to guess as to whether the processed image indicates normal tissue which has been shadowed due to attenuation or whether tissue damage is present.

Thus, it is desirable to develop a method of producing real-time colorized ultrasound images to minimize the possibilities of false diagnoses and, in particular, to identify attenuation and its effects as the imaging occurs.

Therefore, it is an object of the present invention to provide a method of producing real-time colorized ultrasound images that can visually depict attenuation and its effects.

It is another object of the present invention to provide a method of producing real-time colorized ultrasound images that can be easily viewed and analyzed by trained diagnosticians.

It is yet another object of the present invention to provide colorized ultrasound images characterized by a variety of parameters in order to highlight different diagnostic aspects of the patient's organs.

SUMMARY OF THE INVENTION

The present invention is a novel method for producing real-time colorized, contrast enhanced images from a sequence of grey-scale video images. The particular colorizing scheme varies according to which information parameter is desired to be displayed in real-time. The information parameters used to colorize a segment of video images include: time-to-arrival, duration of brightening, and absolute (degree of) brightening.

Time-to-arrival colorization depicts the time that a given pixel achieves a given intensity threshold. A later time to threshold for a given pixel is colored differently than pixels that achieve threshold a predetermined amount of time before or after that later time. Duration of brightening depicts the time that a given pixel's intensity stays above a given threshold. The longer a pixel stays at or above threshold, the pixel is given a different color at certain predetermined time periods. Thus, a pixel of long threshold duration is colored several times during the video image sequence. Absolute brightening depicts various threshold values obtained by the region's pixels. Each color represents a different threshold intensity. Thus, a particularly bright pixel may be colored several times during the course of a video sequence.

One advantage to viewing processed images in real-time is that the patient is still in a position for further testing which can be done immediately in the same session. There is clear benefit to obtaining useful information while the exam is in progress rather than at some later time. Furthermore, the diagnostician can sooner decide on a course of therapy.

Yet another advantage to real-time processing is the detection of attenuation in an imaging session. This is important because attenuation and its effects can also lead to misinterpretation of the data when images are post-processed.

Other features and advantages of the present invention will be apparent from the following description of the preferred embodiments, and from the claims.

For a full understanding of the present invention, reference should now be made to the following detailed description of the preferred embodiments of the invention and to the accompanying drawings.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 2A, 2B, 2C, and 2D depict the problem of attenuation found in ultrasound imaging of posterior regions of the heart.

DETAILED DESCRIPTION OF THE INVENTION

Figure 1A:
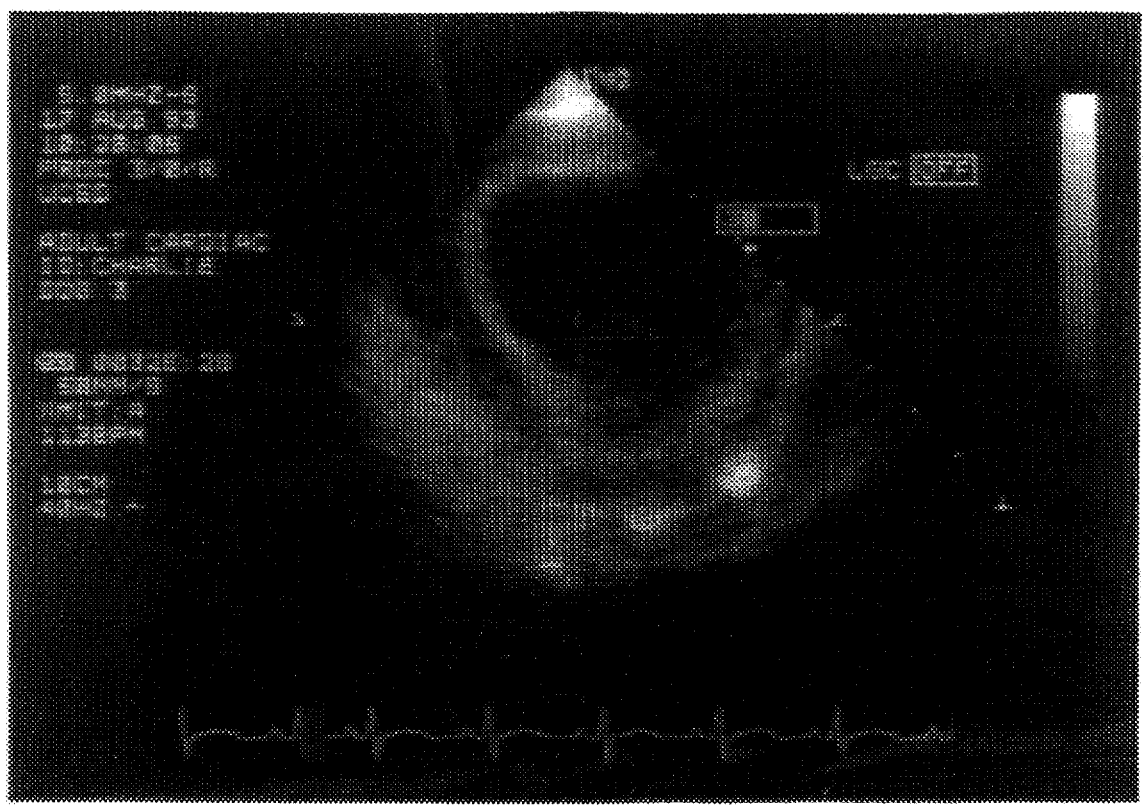
FIG. 1 depicts the attenuation affect as contrast agent enters the chamber of the heart.
Figure 1B:
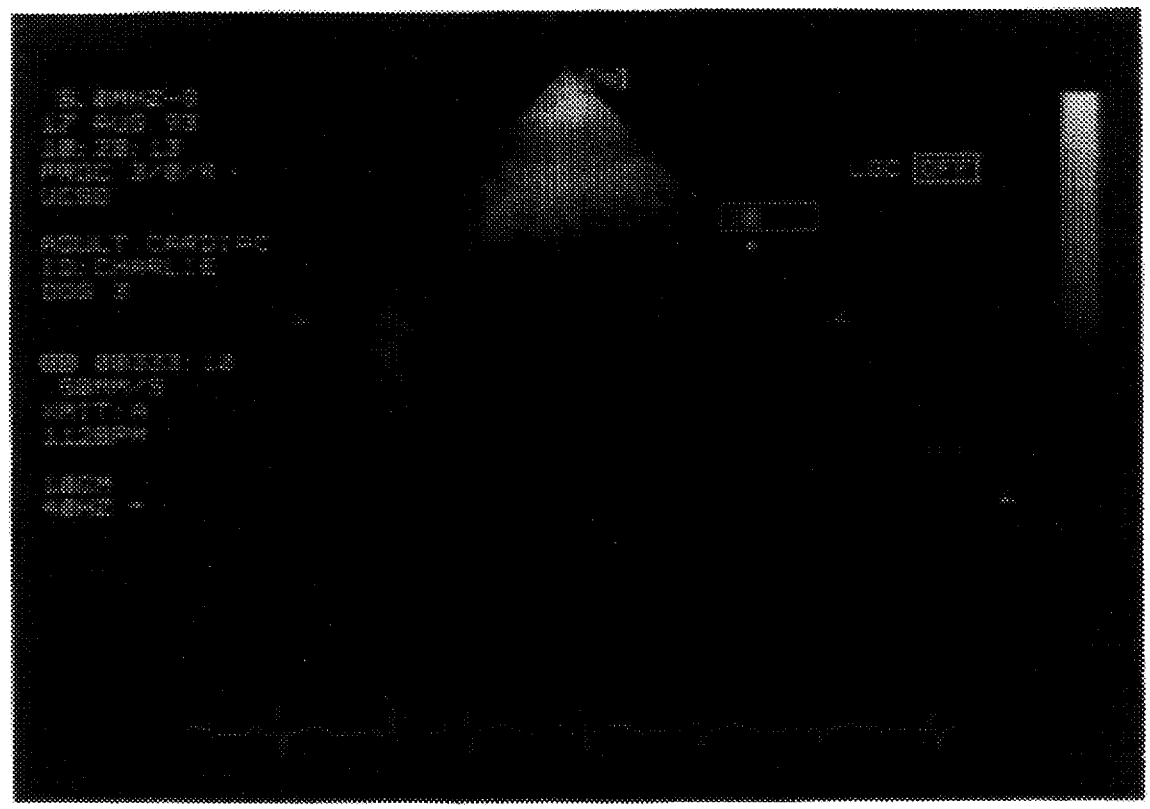

Ultrasound imaging systems are well known in the art. Typical systems are manufactured by, for example, Hewlett Packard Company; Acuson, inc.; Toshiba America Medical Systems, Inc.; and Advanced Technology Laboratories. These systems are employed for two-dimensional imaging. Another type of imaging system is based on three-dimensional imaging. An example of this type of system is manufactured by, for example, TomTec Imaging Systems, Inc. The present invention may be employed with either two-dimensional or three-dimensional imaging systems.

Likewise, ultrasound contrast agents are also well-known in the art. They include, but are not limited to liquid emulsions, solids, encapsulated fluids, encapsulated biocompatible gases and combinations thereof. Fluorinated liquids and gases are especially useful in contrast compositions. The gaseous agents are of particular importance because of their efficiency as a reflector of ultrasound. Resonant gas bubbles scatter sound a thousand times more efficiently than a solid particle of the same size. These types of agents include free bubbles of gas as well as those which are encapsulated by a shell material. The contrast agent may be administered via any of the known routes. These routes include, but are not limited to intravenous (IV), intramuscular (IM), intraarterial (IA), and intracardiac (IC).

It is appreciated that any tissue or organ that receives a flow of blood may have images processed in the manner of the invention. These tissues/organs may include, but are not limited to the kidneys, liver, brain, testes, muscles, and heart.

Numerous parameters may be depicted by the colorization technique. Among the parameters that may be characterized are those of the instantaneous degree of brightening, the integrated degree of brightening, the duration of the brightening, and the time-of-arrival of the contrast agent.

One advantage in showing time-of-arrival data to a trained clinician is to minimize the risk of producing a false negative diagnosis. For example, the post-image capture, colorization methods described by the above articles merely give a final picture depicting which areas of tissue were perfused at any time during the imaging session. Thus, if any tissue in the ROI were experiencing some latent perfusion deficiencies, whereby the arrival of the contrast agent were delayed, this condition would go undetected in the above mentioned methods.

For example, in the case of a critical stenosis or an occlusion of the coronary artery, the "hibernating" myocardial region may receive contrast through a collateral blood supply. In this case, there is a longer path for the contrast agent to reach the myocardial region. The diagnosis of hibernating tissue is critical because it is widely believed that once the occlusion is eliminated, there is an immediate return of normal function. Therefore, the time-of-arrival information would be of significant clinical importance.

A false positive diagnosis might arise because some tissue, even though normally perfused, might appear shadowed due to the effect of attenuation. Thus, a trained diagnostician might falsely conclude that the tissue is functioning outside normal parameters, when the problem is merely the result of the attenuation effect.

Furthermore, by colorizing based on data from a region which may have portions affected by attenuation and shadowing, colors may be derived that do not truly reflect the contrast perfusion. Without such real-time, dynamic data, it is possible that even a trained diagnostician might falsely conclude that the tissue is functioning in a particular manner, either normally or abnormally. In these methods, there lies risk for both false negative and false positive diagnoses. Real-time colorization avoids these dangers.

EXAMPLE—Myocardial Contrast Echocardiography

Figure 3:
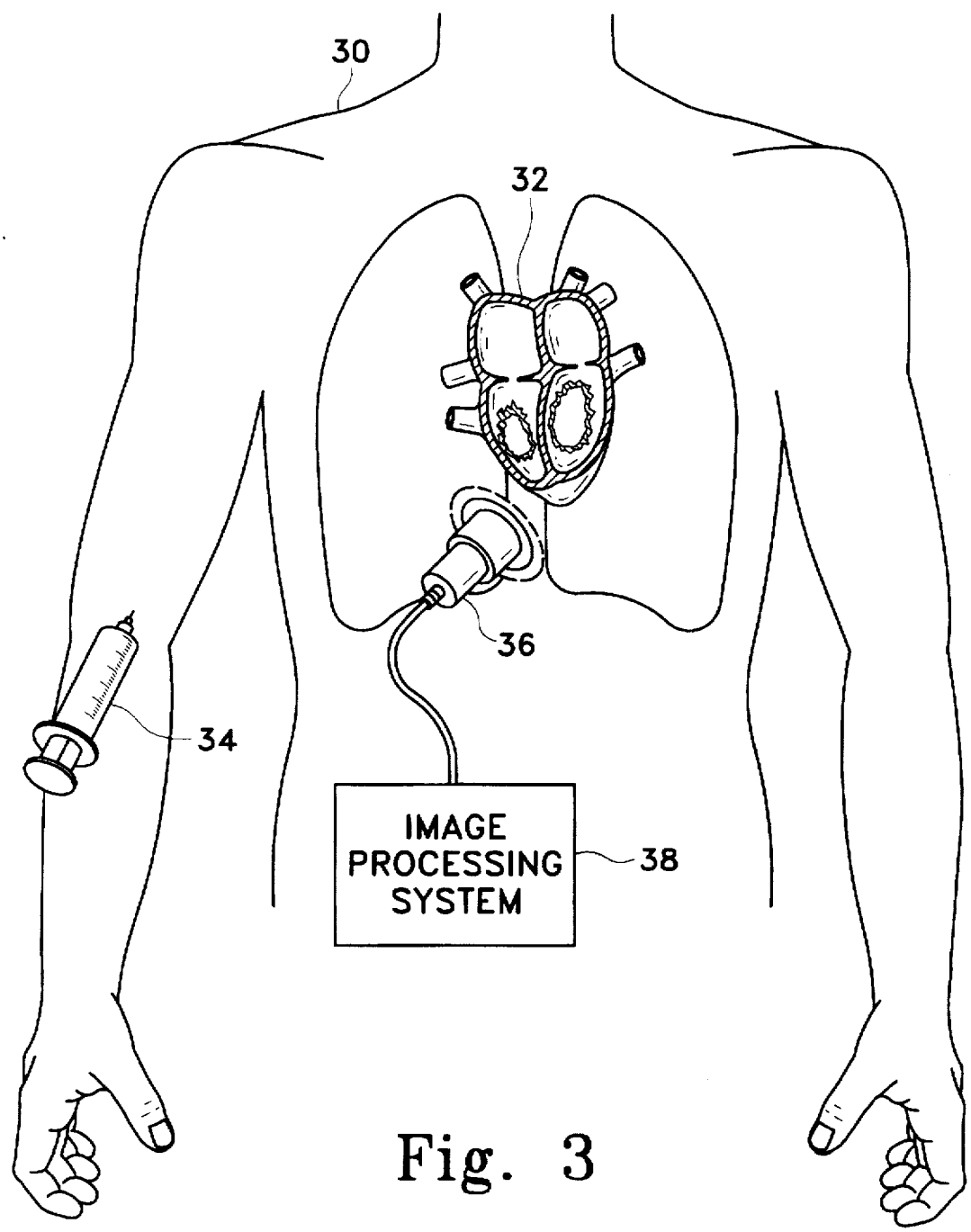
FIG. 3 depicts the manner in which ultrasound images are taken of a patient's heart by an ultrasound image processor that is used in accordance with the principles of the present invention.

Referring now to FIG. 3, a cut-away view of patient 30 attached to echocardiographic transducer 36 is shown. A transducer is placed on the patient, proximate to heart muscle 32. An injection (34) of contrast agent is made into the patient's vein so that the contrast agent reaches the heart and interacts with the ultrasound waves generated by transducer 36. Sound waves reflected and detected at transducer 36 are sent as input into image processing system 38.

As the contrast agent enters into various heart regions, image processing system 38 detects an increased amplitude in the reflected ultrasound waves, which is characterized by a brightening of the image. Tissue areas that do not brighten when expected may indicate a disease condition in the area (e.g. poor or no circulation, necrosis or the like).

Figure 4:
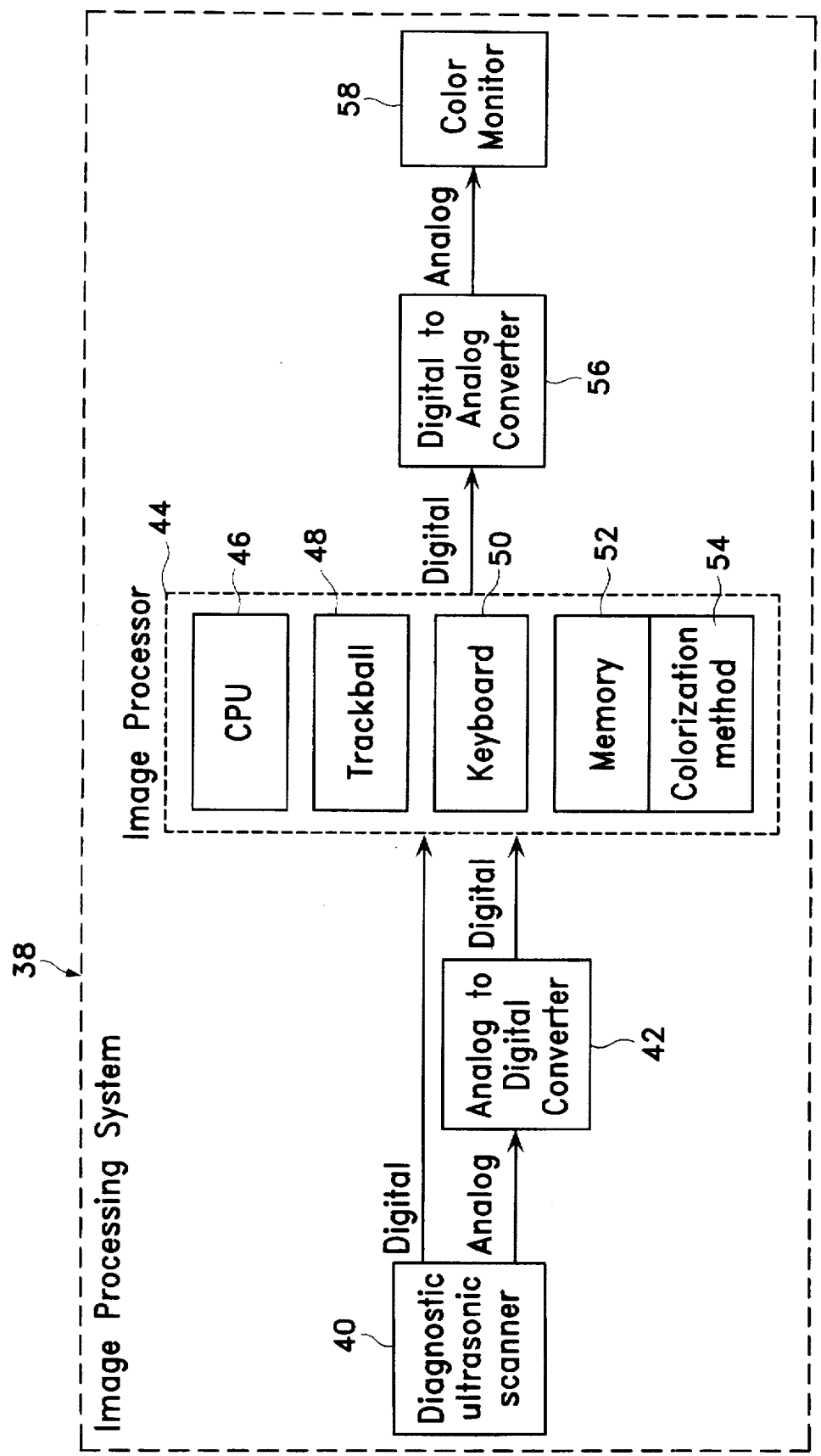
FIG. 4 is a high level block diagram of one embodiment of an image processor unit that is used in accordance with the principles of the present invention.

Referring now to FIG. 4, an embodiment, in block diagram form, of image processing system 38 is depicted. Image processing system 38 comprises diagnostic ultrasound scanner 40, optional analog-to-digital converter 42, image processor 44, digital-to-analog converter 56, and color monitor 58. Ultrasound scanner 40 encompasses any means of radiating ultrasound waves to the region of interest and detecting the reflected waves. Scanner 40 could comprise transducer 36 and a means of producing electrical signals in accordance with the reflected waves detected. It will be appreciated that such scanners are well known in the art.

The electrical signals generated by scanner 40 could either be digital or analog. If the signals are digital, then the current embodiment could input those signals into image processor 44 directly. Otherwise, an optional A/D converter 42 could be used to convert the analog signals.

Image processor 44 takes these digital signals and processes them to provide real-time colorized video images as output. The current embodiment of image processor 44 comprises a central processing unit 46, trackball 48 for user-supplied input of predefined regions of interest, keyboard 50, and memory 52. Memory 52 may be large enough to retain several video images and store the colorization method 54 of the present invention. CPU 44 thus colorizes video images according to stored colorization method 54.

After a given video image is colorized by image processor 44, the video image is output in digital form to D/A converter 56. D/A converter thereby supplies color monitor 58 with an analog signal capable of rendering on the monitor. It will be appreciated that the present invention could alternatively use a digital color monitor, in which case D/A converter 56 would be optional.

Figure 5:
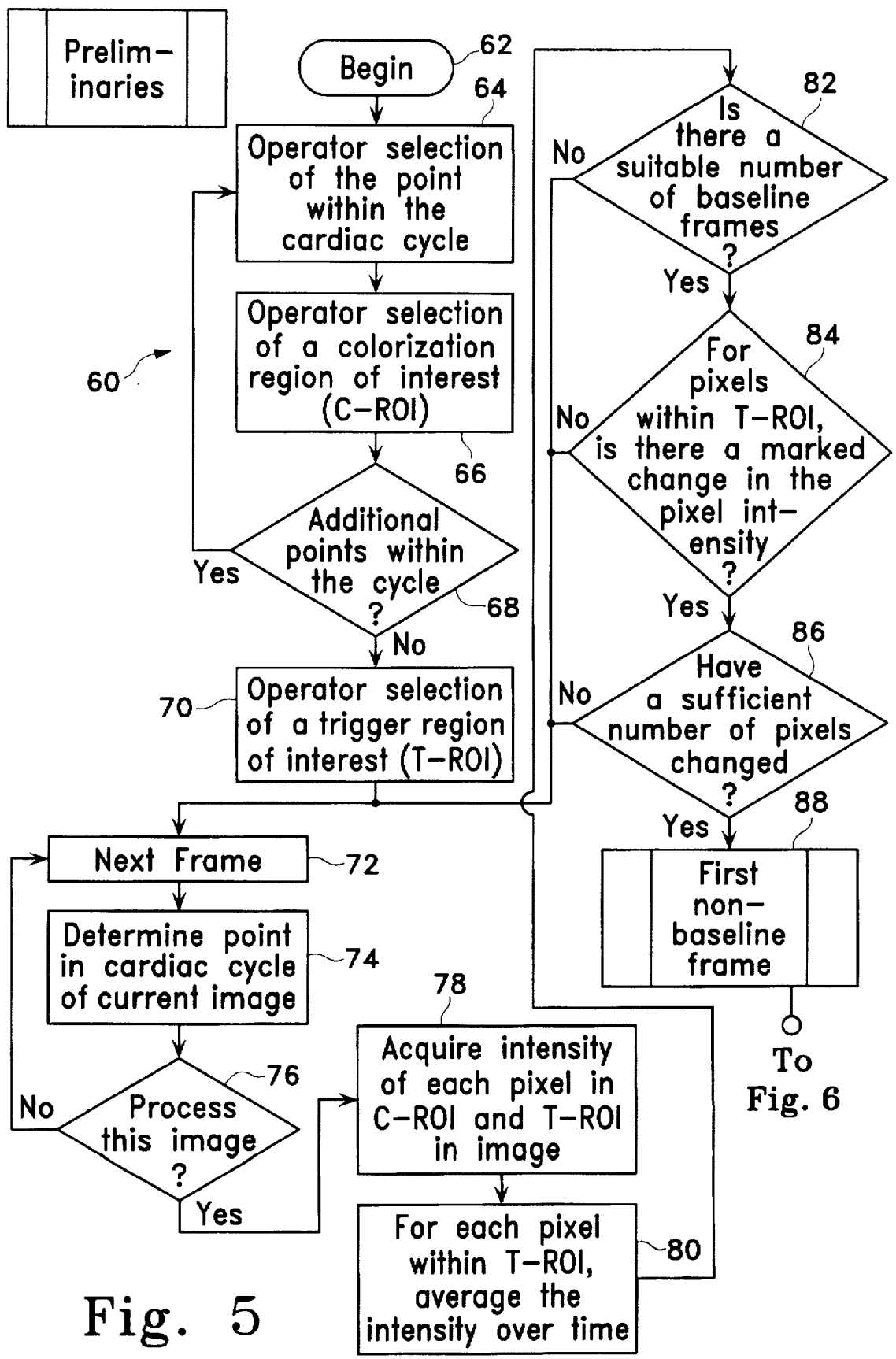
FIGS. 5–7 depict a flow chart of the presently claimed real-time colorization method.
Figure 6:
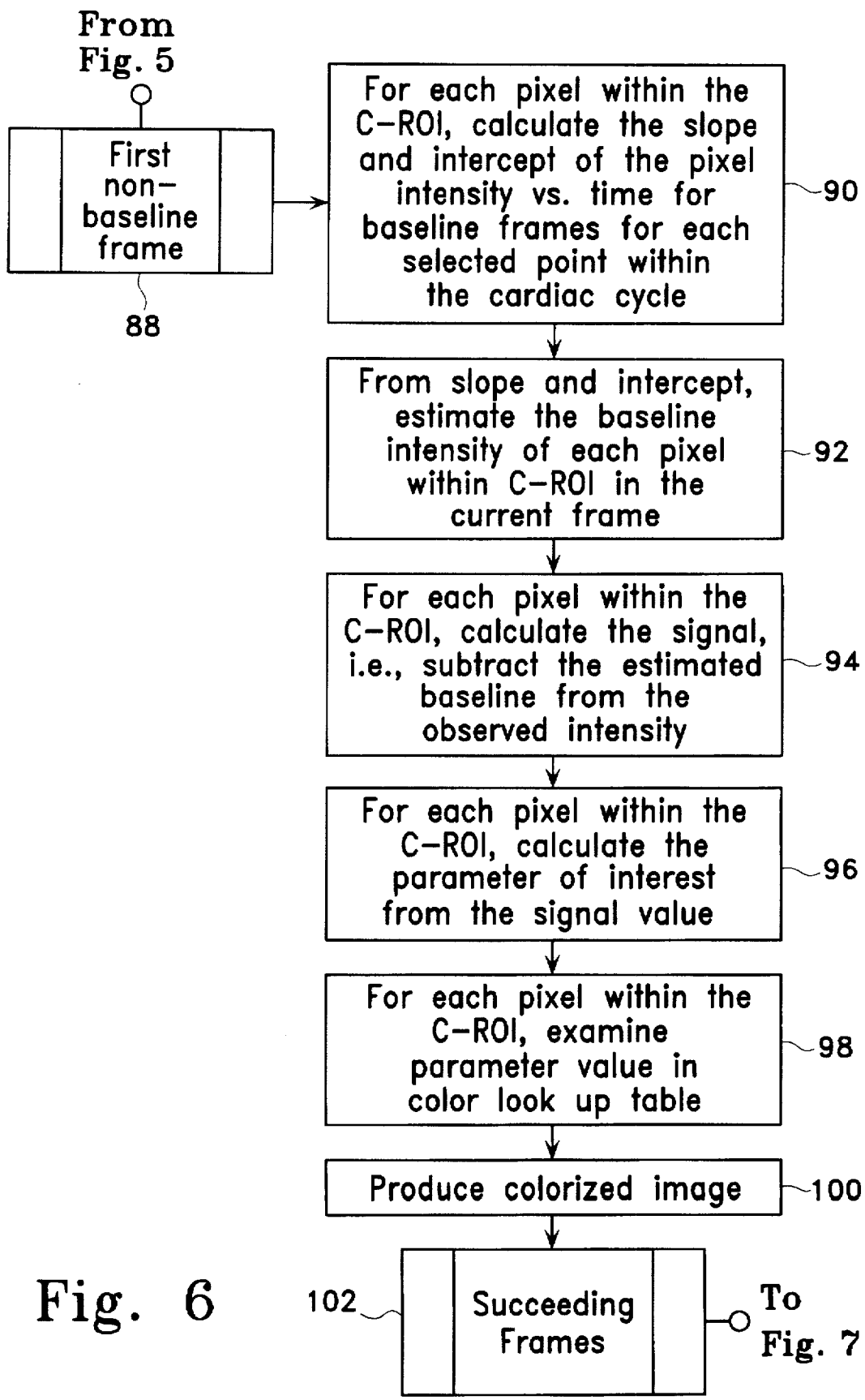
Figure 7:
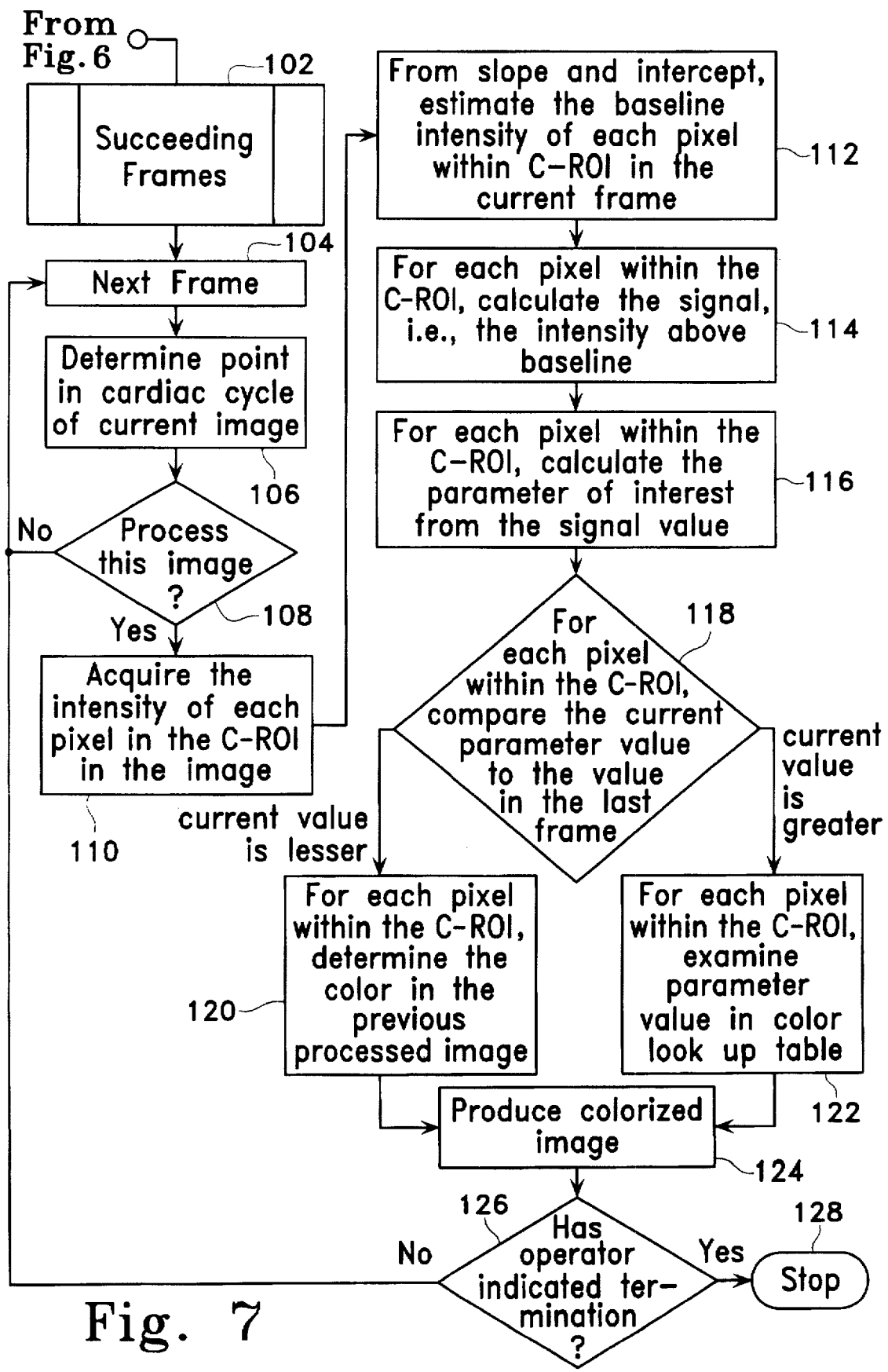

Having described a current embodiment of the present invention, the colorization method of the present invention will now be described. FIGS. 5–7 are flowcharts describing the colorization method as currently embodied. Preliminary processing begins in FIG. 5 at step 62. The operator-user selects which point in the cardiac cycle at which the series of video images will be taken. The same point in the cycle is used to reduce the amount of heart distortion from frame to frame because the heart is presumably in the same place at the same point in the cardiac cycle. Of all the point in the cardiac cycle, the most frequently used are the end-systolic and the end-diastolic points.

The operator then selects the region of interest to be colorized (C-ROI) in the heart at step 66. This may be accomplished by allowing continuous scanning of the heart prior to administering the contrast agent and having the operator select the C-ROI on screen with trackball 48. Once selected, the current method allows other points on the cycle to be included in the analysis at step 68.

Once all the point on the cycle and C-ROI's have been identified, the operator selects a "trigger" region of interest (T-ROI) that is used to identify that the contrast agent has or will be imminently entering entered the region of interest. For assessing myocardial perfusion, a most advantageous T-ROI would be somewhere in the heart chamber because the heart chamber receives the contrast agent prior to the muscle. For examining the left ventricle, the T-ROI may be in the right ventricle or the left atrium. Once the T-ROI is selected, the heart continues to be imaged frame-by-frame.

As each frame is acquired, the current method determines whether the current frame is one of the pre-identified points of the cardiac cycle. This may be accomplished by performing an electrocardiogram (ECG) on the patient at the same time that the image sequence is being captured. The ECG could then be used to supply steps 74 and 76 the data needed to determine the exact point in the cardiac cycle.

If the current frame is processed at step 78, the intensity of each pixel is acquired in the C-ROI and the T-ROI. This intensity pixel data is stored and used to compute an average intensity over several baseline frames. In the current method, two or three baseline frames are used and that number is tested in step 82.

At steps 84 and 86, the current method waits until there is a marked change in intensity in a sufficient number of pixels in the T-ROI. This change denotes that the contrast agent has been administered and that the next frame is the first non-baseline frame. The first non-baseline frame is processed at step 90 in FIG. 6. In step 90, for each pixel in the C-ROI, a slope and intercept of pixel intensity vs. time for the baseline frames is calculated. From this slope and intensity, the baseline intensity for the current frame is estimated in step 92.

This method to estimate the baseline intensity for post-contrast frames uses the intensity from pre-contrast frames. The intensity from pre-contrast frames may be simply averaged to obtain a value for baseline frames that is constant for all succeeding frames. A simple average may not be sufficient in some cases to characterize the baseline as some changes in the pixel intensity may occur prior to the arrival of contrast. These changes may arise, for example, from poor image registration caused by changes in the transducer position and/or the motion of the heart or the ROI may be adjacent to a region where contrast has arrived (e.g. the septal region of the myocardium lying next to the right ventricle, which receives a high concentration of contrast prior to the left ventricle). In these cases, the baseline intensity is better represented by a line, which assumes that the changes will continue over time, incorporating a time dependence on the baseline intensity.

With the baseline intensity calculated for each pixel, the pixel intensity is calculated by subtracting the estimated baseline from the observed intensity. Once the pixel intensity has been calculated, the parameter of interest is then calculated in step 96. As will be discussed below, the parameter of interest may be one of many that relate the intensity of the pixel into the time of the observed intensity. Currently, these parameters include: time-to-arrival data, duration of brightening, and absolute brightening.

For each pixel in the C-ROI, the calculated parameter is used to find the particular color that the pixel receives in the current frame. The particular color may be found in a color look-up table. In this manner, a colorized image frame is produced for the first non-baseline frame in step 102. This first colorized frame produces an initial coloring for each pixel that subsequent frames may change.

Succeeding frames are processed starting at step 104 in FIG. 7. Again, the image sequence is tested for images that occur at the same point in the cardiac cycle at steps 106 and 108. If the frame is to be processed, pixel intensity is acquired, a new pixel baseline is estimated, the pixel intensity is baseline subtracted, and the parameter of interest is calculated in steps 110 through 116. At step 118, the current pixel intensity is compared with the intensity in the last frame. If the current intensity value is less, then the previous color is determined in step 120. If greater, a new color is looked-up in the table. In this manner, subsequent frames are colorized and produced in step 124. Lastly, the current method looks for user-supplied termination in step 126 to complete the colorization process.

To gain a better understanding of the application of the above-described colorization method, FIGS. 8A–8F show a series of six frames that have been colorized using the time-to-arrival parameter. Thus, individual pixels are colored when they meet or exceed a certain intensity threshold at a specific time—otherwise the pixel remains uncolored. Under the current embodiment of this parameter, pixels are colored yellow if they exceed threshold within a certain time, $t_1$; green if they have exceeded threshold between time $t_1$ and another time $t_2$; blue if threshold occurs between $t_2$ and a later time $t_3$; and red if threshold occurs between $t_3$ and a later time $t_4$.

FIGS. 8A–8F also depicts how the real-time colorized image processing of the present invention can make visual for the diagnostician the effects of attenuation. This particular series of real-time colorized images of exhibits both the effects of attenuation and a possible disease condition in the patient's heart.

Figure 8A:
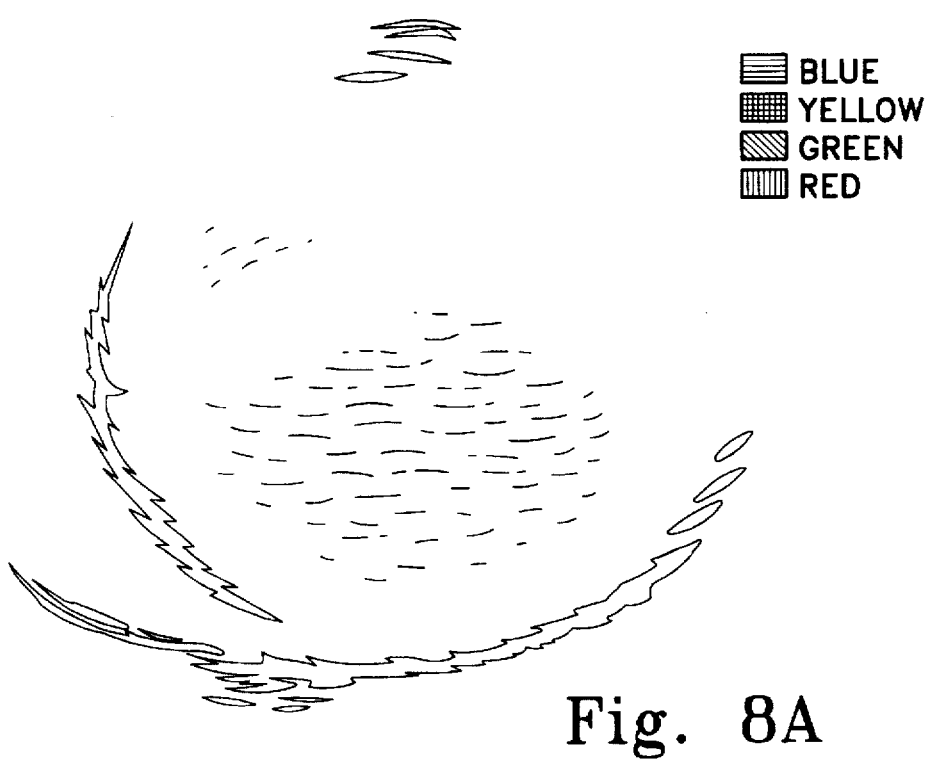
FIGS. 8A–8F depict the real-time colorization of a patient's heart using the "time-of-arrival" parameter.
Figure 8B:
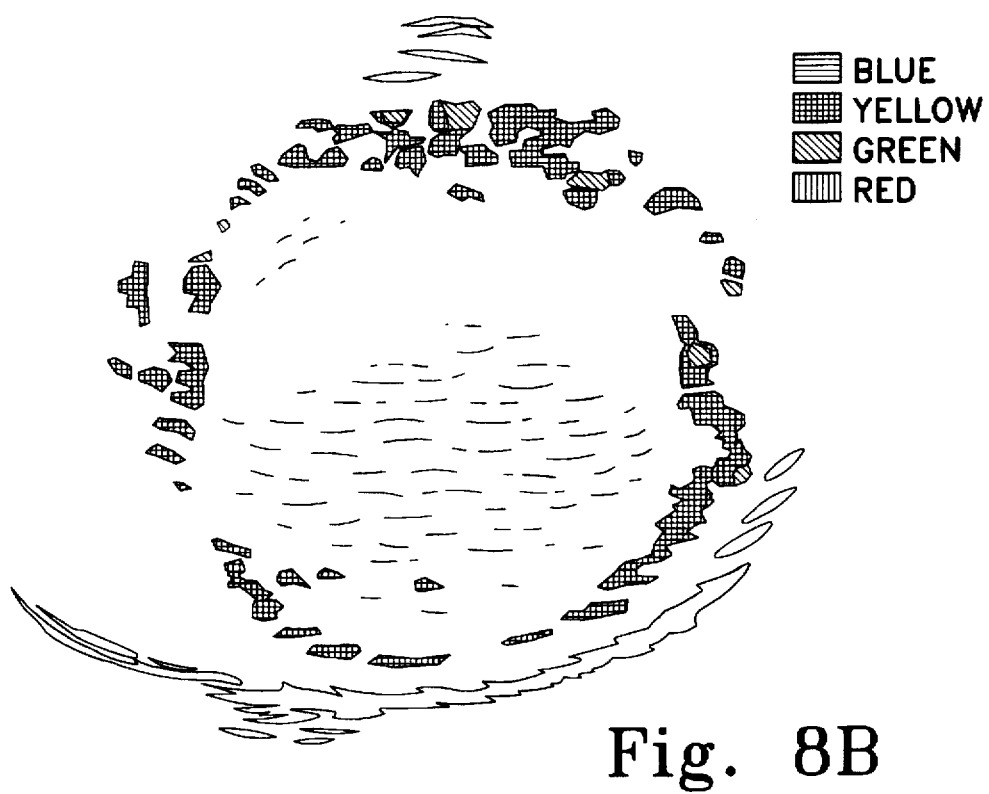

FIG. 8A is the first frame in the series and is taken prior to the arrival of the contrast agent; thus, no color is added to the frame. At the time of FIG. 8B, time has elapsed to somewhere between $t_1$ and $t_2$, as defined above, because the colors yellow and green are now visible. At this time, it is clear that perfusion all around the heart muscle is occurring—even in the posterior region of the heart, since some of the posterior area has been colored yellow. It should be noted that because the color yellow is fairly well distributed about the heart muscle, the effects of attenuation are not yet present.

Figure 8C:
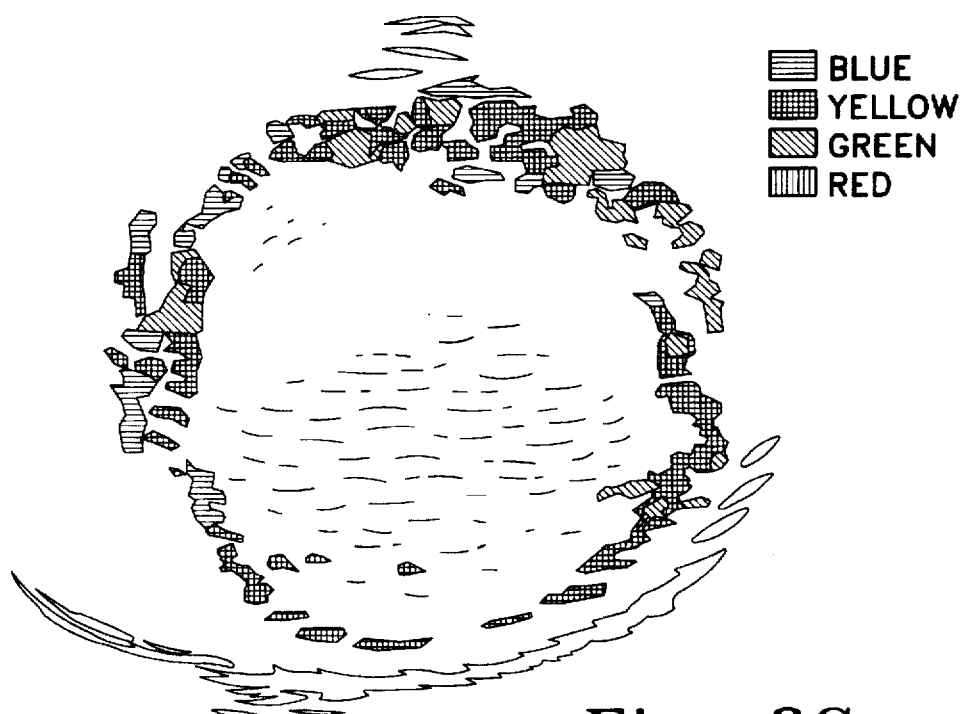

By the time of FIG. 8C (i.e. somewhere between $t_2$ and $t_3$), the effects of attenuation are beginning to show. The colors blue and green are now predominant in the hemisphere anterior to the heart chamber; whereas the posterior hemisphere is largely yellow or uncolored. Also noted in FIG. 8C is a potentially diseased region to the right of the heart chamber and in the anterior hemisphere—this region remains uncolored.

Figure 8D:
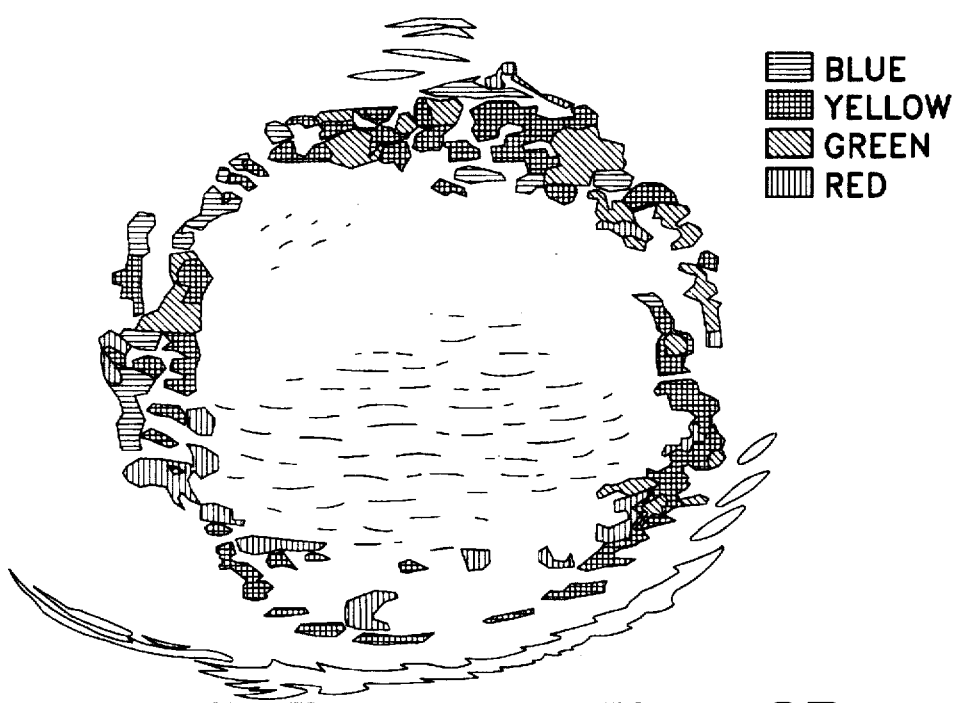
Figure 8E:
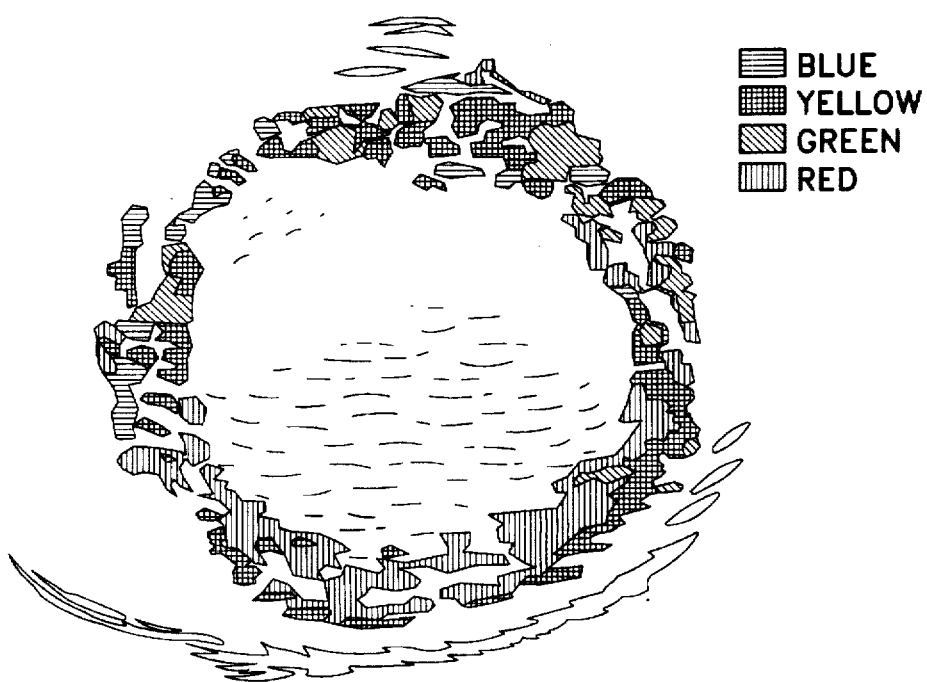
Figure 8F:
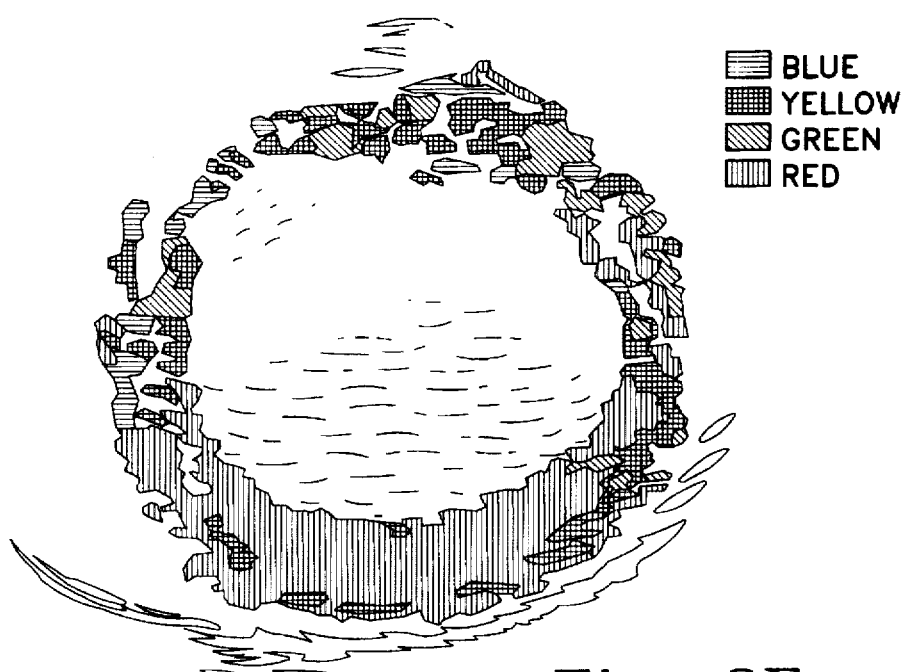

In FIG. 8D, the current time is somewhere after $t_4$, as the color red has now appeared. As the red predominates in the posterior region, together with some uncolored pixels, the region is still "shadowed" by agent in the heart chamber. Both FIGS. 8E and 8F are likewise after time $t_4$. By the time of FIG. 8F, the vast majority of the posterior region is colorized—with red as predominant color. This coloring pattern is consistent with the expected effects of attenuation and is made plainly visual to the diagnostician.

Additionally noted in FIGS. 8E and 8F, the right lateral region has been colorized red. This red colorization cannot be explained away as due to the effects of attenuation. The only other plausible explanation for the late "time-to-arrival" threshold is that there is some restriction in the flow of blood to this particular region—potentially a diseased condition.

The images presented in FIGS. 8A–8F are frames that have been chosen from the real-time moving video sequence for purposes of representing the salient aspects of the invention. It can be appreciated that the present invention lies in viewing the video image as a flowing sequence of colorized frames appearing on the monitor in real-time.

Figure 9:
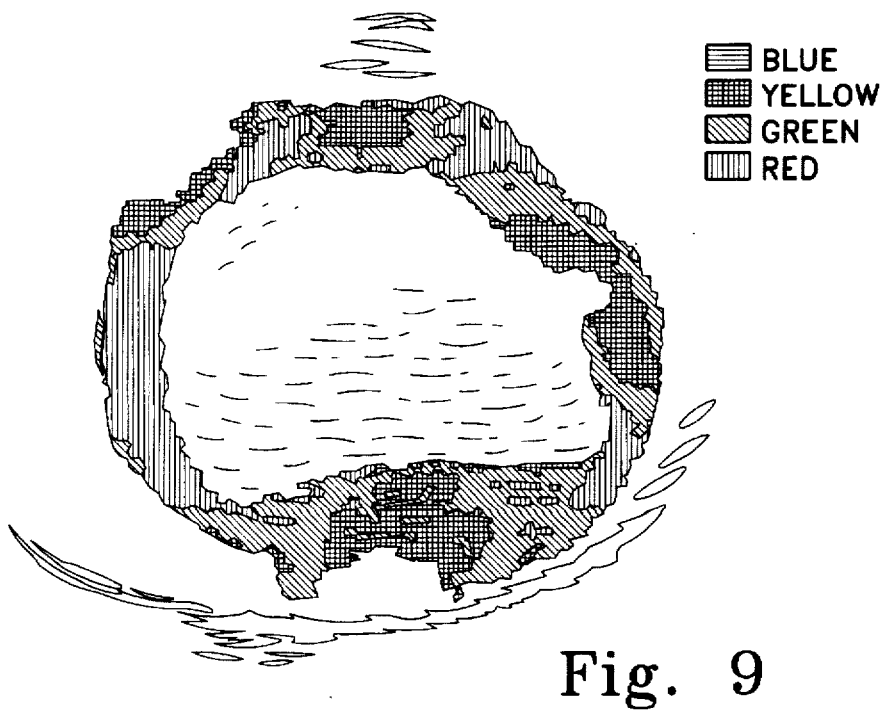
FIG. 9 depicts a single frame of a real-time colorized image according to the "duration of brightening" parameter without the left ventricle colorized.

Other parameters are similarly depicted. FIG. 9 depicts a single frame in a sequence of real-time images colorized according to the "duration of brightening" parameter. As noted, this particular color scheme uses color to denote how long a given pixel was above a certain threshold. If the period of time is long, the color of the pixel is red. If the pixel was at or above the threshold for only a short period of time, the color is blue.

Figure 10:
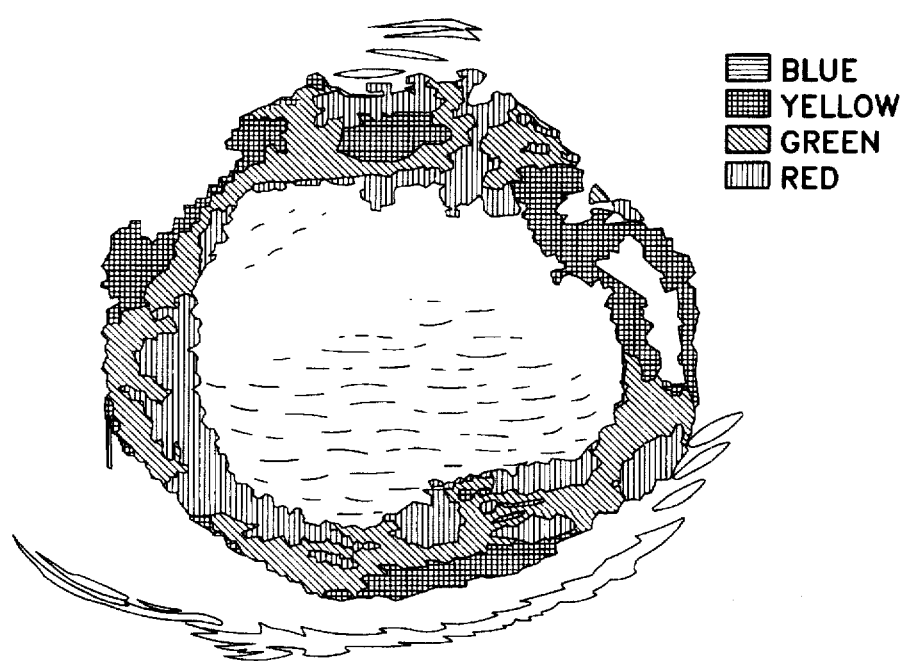
FIG. 10 depicts an end-systolic real-time image frame colorized according to the "absolute brightening" parameter without the left ventricle colorized.
Figure 11:
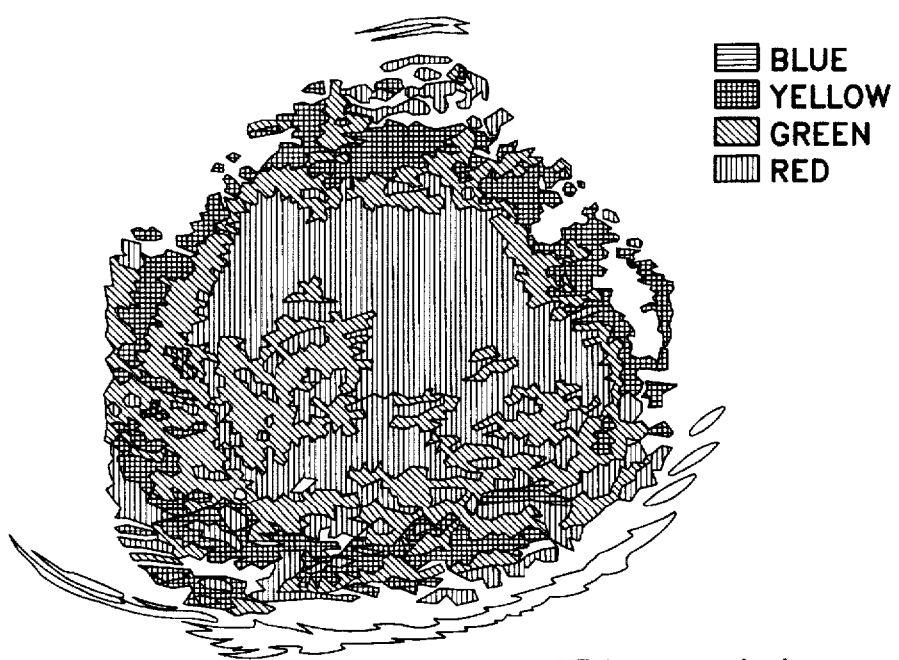
FIG. 11 depicts an end-diastolic real-time image frame colorized according to the "absolute brightening" parameter with the left ventricle colorized.

FIGS. 10 and 11 both depict a frame colorized according to the "absolute brightening" parameter. Absolute brightening colors a particular pixel according to the level of intensity it has achieved. This may be accomplished by predefining a set of threshold levels that are assigned different colors. If the given pixel meets a given threshold, it is assigned that particular color. The color is reassigned only if the pixel exceeds another threshold.

It will be noted that, in some frames, the left ventricle chamber is not colorized. In some cases, it may be desirable to color the left ventricle. For example, FIG. 10, is an end-systolic frame without the left ventricle colored; whereas FIG. 11 is an end-diastolic frame with the left ventricle colored.

Although only four parameters have been discussed in connection with the present colorization method, it will be appreciated that more parameters that relate pixel intensity to a time element is possible and that the present invention should not be limited to the above-described parameters. Indeed, the present invention should be construed to cover any parameter that is reasonably compatible with the above-described colorization method.

There has thus been shown and described a novel method for the processing of real-time contrast enhanced, colorized images which meets the objects and advantages sought. As stated above, many changes, modifications, variations and other uses and applications of the subject invention will, however, become apparent to those skilled in the art after considering this specification and accompanying drawings which disclose preferred embodiments thereof. All such changes, modifications, variations and other uses and applications which do not depart from the spirit and scope of the invention are deemed to be covered by the invention which is limited only by the claims which follow.

I claim:

1. A method of colorizing corresponding points in a region of interest of a subject in a series of grey-scale ultrasound images comprising:
    a) commencement of grey scale imaging of the region of interest of the subject;
    b) administration of contrast agent to the subject wherein the contrast agent perfuses to the region of interest;
    c) for the first image to be colorized, colorize each corresponding point according to the results of a comparison between a parameter and the value of the reflected signal of the corresponding point; and
    d) for each subsequent image in the series, colorizing each corresponding point according to the results of a comparison made between a parameter, the value of the reflected signal from the corresponding point in the image and a previous non-baseline value of the reflected signal of the corresponding point.

2. The method of claim 1 wherein the contrast agent is chosen from the group consisting of liquid emulsions, solids, encapsulated fluids, encapsulated biocompatible gases and combinations thereof.

3. The method of claim 2 wherein the contrast agent comprises a fluorinated gas or liquid.

4. The method of claim 1 wherein the imaging is performed two-dimensionally.

5. The method of claim 1 wherein the imaging is performed three-dimensionally.

6. The method of claim 1 wherein said parameter is the time of arrival of the contrast agent.

7. The method of claim 1 wherein said parameter is the instantaneous degree of brightening of the tissue as a result of the arrival of the contrast agent.

8. The method of claim 1 wherein said parameter is the integrated degree of brightening of the tissue as the result of the arrival of the contrast agent.

9. The method of claim 1 wherein said parameter is the duration of the brightening by the contrast agent as it remains in the tissue.

10. The method of claim 1 wherein each said corresponding point is a pixel.

11. A method of diagnosing tissue/organ condition comprising:
    a) commencement of grey scale imaging to obtain at least one baseline image;
    b) administration of contrast agent to the subject for the obtainance of non-baseline images;
    c) processing of images by colorization in real-time, wherein the colorization is made to corresponding points in said images in accordance with a parameter and two values of the reflected signal at the corresponding points, wherein one said value is derived from the current image being processed and the other said value is selectable from the set of baseline and non-baseline images; and
    d) analyzing the colorized images.

12. The method of claim 11 wherein contrast agent is chosen from the group consisting of liquid emulsions, solids, encapsulated fluids, encapsulated biocompatible gases and combinations thereof.

13. The method of claim 12 wherein the contrast agent comprises a fluorinated gas or liquid.

14. The method of claim 11 wherein the imaging is performed two-dimensionally.

15. The method of claim 11 wherein the imaging is performed three-dimensionally.

16. The method of claim 11 wherein said parameter is the time of arrival of the contrast agent.

17. The method of claim 11 wherein said parameter is the instantaneous degree of brightening of the tissue as a result of the arrival of the contrast agent.

18. The method of claim 11 wherein said parameter is the integrated degree of brightening of the tissue as the result of the arrival of the contrast agent.

19. The method of claim 11 wherein said parameter is the duration of the brightening by the contrast agent as it remains in the tissue.

20. The method of claim 11 wherein the tissue being diagnosed comprises the heart.

21. The method of claim 20 wherein the processing is performed at more than one point in the cardiac cycle.

22. The method of claims 20 or 21 wherein the colorization includes the left ventricle region.

23. The method of claims 20 or 21 wherein the colorization does not include the left ventricle region.

24. The method of claim 11 wherein the tissue being diagnosed comprises kidney.

25. The method of claim 11 wherein the tissue being diagnosed comprises the brain.

26. The method of claim 11 wherein the tissue being diagnosed comprises the liver.

27. The method of claim 11 wherein the tissue being diagnosed comprises the testes.

28. The method of claim 11 wherein the tissue being diagnosed comprises muscle tissue.

29. The method of claim 11 wherein the tissue being diagnosed comprises the blood flow within tissue/organ.

30. The method of claim 11 wherein the processing is performed at more than one point in the cardiac cycle.

31. The method of claim 11 wherein each said corresponding point is a pixel.

32. A method for producing a series of real-time colorized images of corresponding points in a region of interest, said images taken with an ultrasound diagnostic scanning apparatus or an ultrasound image processing apparatus wherein the apparatus processes the series of grey scale images according to a pre-determined parameter; the steps of the method comprise:

(a) identifying a region of interest in the images for processing;

(b) for the first grey scale image in the series,
  (i) determining the value of the reflected signal of the corresponding point;
  (ii) colorizing the corresponding point based upon a comparison of the pre-determined parameter and the value determined in step (b)(ii).

(c) for each subsequent grey scale image,
  (i) determining the value of the reflected signal of the corresponding point in the current image;
  (ii) colorizing the corresponding point based upon a comparison of the pre-determined parameter, the value of the reflected signal of the corresponding point in the current image and the value of the reflected signal of the corresponding point in a previous image, wherein such previous image is selectable from the set of baseline and non-baseline images.

33. The method of claim 32 wherein the method further comprises two-dimensional imaging.

34. The method of claim 32 wherein the method further comprises three-dimensional imaging.

35. The method of claim 32 wherein said parameter is the time of arrival of contrast agent.

36. The method of claim 32 wherein said parameter is the instantaneous degree of brightening of the region of interest as a result of the arrival of contrast agent.

37. The method of claim 32 wherein said parameter is the integrated degree of brightening of the region of interest as the result of the arrival of contrast agent.

38. The method of claim 32 wherein said parameter is the duration of brightening by the contrast agent as it remains in the region of interest.

* * * * *